United States Patent [19]

Beregi et al.

[11] 4,161,529
[45] Jul. 17, 1979

[54] PHENOXY PHENYL PYRROLIDINE COMPOUNDS, COMPOSITIONS AND METHODS OF USE

[75] Inventors: Laszlo Beregi, Boulogne; Pierre Hugon, Rueil-Malmaison; Jacques Duhault, Chatou; Michèlle Boulanger, Marly le Roi, all of France

[73] Assignee: Science Union et Cie, Societe Francaise de Recherche Medicale, Suresnes, France

[21] Appl. No.: 877,601

[22] Filed: Feb. 14, 1978

[30] Foreign Application Priority Data

Feb. 25, 1977 [GB] United Kingdom ............... 8096/77

[51] Int. Cl.² .................... A61K 31/40; C07D 207/06
[52] U.S. Cl. ...................................... 424/274; 560/39; 260/307 A; 260/326.43; 260/326.5 M; 260/326.5 R; 260/544 P
[58] Field of Search .................... 260/326.43; 424/274

[56] References Cited
FOREIGN PATENT DOCUMENTS
1549152 12/1968 France.

Primary Examiner—Donald G. Daus
Assistant Examiner—Lisa Jones
Attorney, Agent, or Firm—Omri M. Behr

[57] ABSTRACT

Pyrrolidone derivatives of the formula:

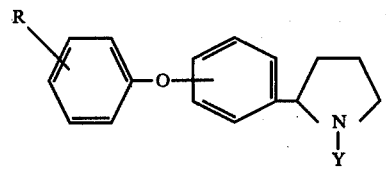

wherein
R is hydrogen, halogen, lower alkyl, lower alkoxy or trifluoromethyl,
and
Y is hydrogen, saturated or unsaturated hydrocarbon radical up to $C_4$, hydroxyethyl, hydroxypropyl or carboxymethyl.

These compounds are used as medicines especially in the treatment of lipid-metabolism disorders.

9 Claims, No Drawings

PHENOXY PHENYL PYRROLIDINE COMPOUNDS, COMPOSITIONS AND METHODS OF USE

The present invention provides pyrrolidine derivatives of the formula I

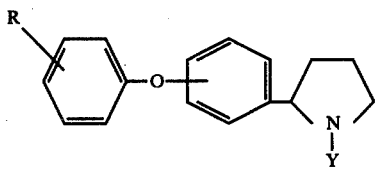

wherein:
R is selected from the group consisting of a hydrogen atom, halogen atoms, such for example as chlorine and fluorine atoms, alkyl and alkoxy radicals each having from 1 to 4 carbon atoms inclusive and trifluoromethyl radical;
Y is selected from the group consisting of a hydrogen atom, saturated and unsaturated hydrocarbon radicals containing from 1 to 4 carbon atoms inclusive, such for example as methyl, ethyl, propyl, butyl, allyl, methylallyl and propinyl groups, a hydroxyethyl radical, a hydroxy propyl radical and a carboxymethyl radical.

The present invention also provides acid addition salts, especially physiologically tolerable acid addition salts, of the compounds of the formula I. As acids which may be used for the formation of these salts, there may be mentioned for example, in the mineral series: hydrochloric, hydrobromic, sulfuric and phosphoric acids, and in the organic series: acetic, propionic, maleic, fumaric, tartaric, citric, oxalic, benzoic, methanesulfonic and isethionic acids.

The present invention provides a process for preparing compounds of the formula I which comprises reducing a compound of the formula II:

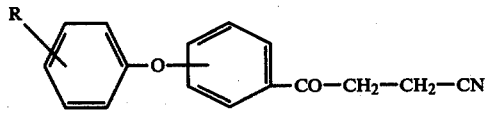

wherein R has the meaning previously given, with hydrogen under pressure in the presence of a hydrogenation catalyst, in order to obtain a compound of the formula:

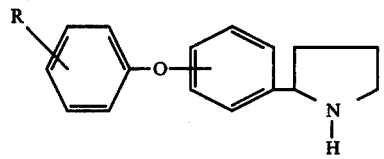

wherein R has the meaning previously given, and if desired, treating this last compound by classical chemical methods to obtain the corresponding N-substituted pyrrolidine of the formula I wherein R has the meaning given above and Y represents a saturated or unsaturated hydrocarbon radical having from 1 to 4 carbon atoms inclusive, a hydroxyethyl, hydroxypropyl or carboxymethyl radical.

The reduction step of the process is advantageously carried out under a hydrogen pressure of about 8 $kg/cm^2$ in the presence of Raney Nickel as the catalyst; the reduction is carried out in a suitable solvent for example dimethyl formamide, at a temperature of from 50° to 80° C.

The methods used to prepare the N-substituted pyrrolidines of the formula I from the corresponding N-unsubstituted pyrrolidines are the classical chemical methods generally used to bound an alkyl, alkenyl, hydroxyalkyl or carboxyalkyl radical to the nitrogen atom of a secondary amine.

The starting compounds of the formula II are prepared according to the method of W. Steglich and P. Gruber, Angew. Chem. 83, 727 (1971) starting from the phenoxy benzoic acids of the formula A:

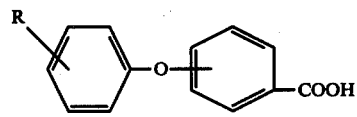

wherein R has the meaning given above. This method, described in the examples, may be schematized as follows:

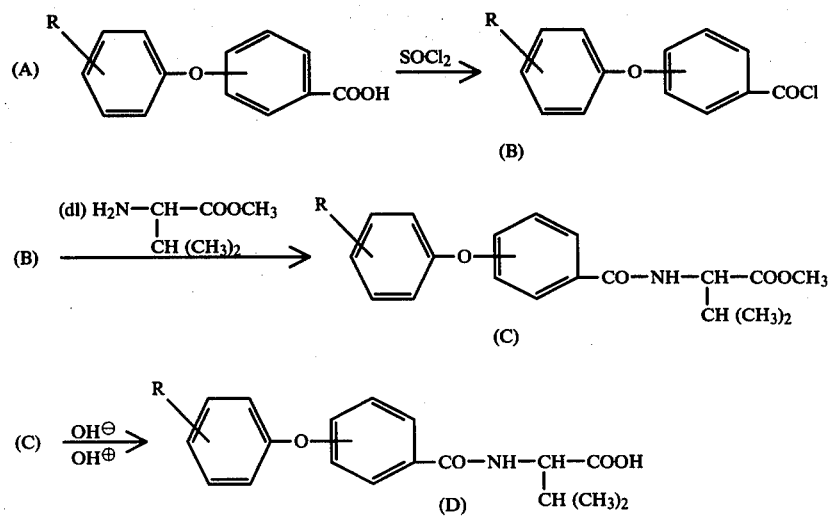

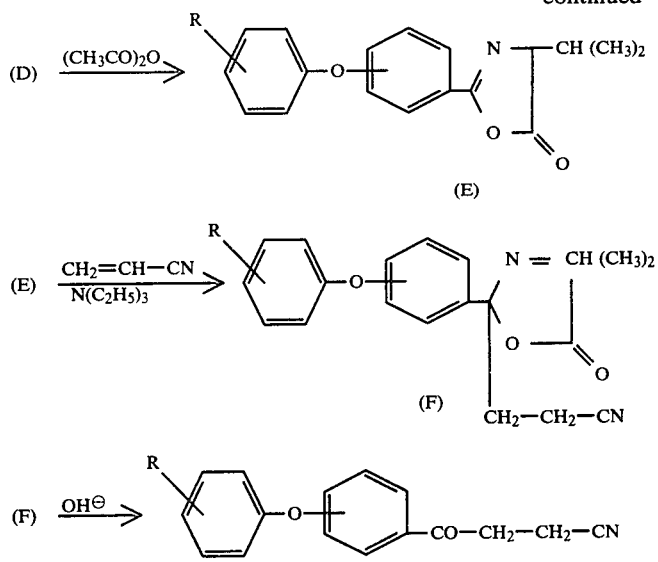

R having in these formulae the same meaning as in formula I.

The compounds of the formula I and physiologically tolerable salts thereof possess valuable pharmacological and therapeutic properties, especially lipid-metabolism regulating properties. They may, therefore, be used as medicines especially in the prevention and treatment of lipid-metabolism disorders which may be either genetic disorders or dyslipemia secondary to glucids abnormalities, contraceptive pills, diabetes and obesity. So, they may be used for preventing or treating hyperlipidemia, obesity and atherosclerosis.

Their toxicity is low and their $LD_{50}$ determined in mice is within the range of 400 to 1000 mg/kg by the oral route or of 50 to 400 mg/kg by the intraperitoneal route.

The activity of the compounds of the present invention on lipid-metabolism was evidenced in the rats submitted to different diets.

The compounds of the present invention were administered to rats receiving a lipid increased food for a period of four days at daily doses which may vary from 5 to 25 mg/kg P.O. according to the compounds.

The animals were killed two hours after the last administration. There was then observed a decrease of the plasma triglycerides level up to 76% by comparison with untreated animals.

Similarly, the compounds of the present invention were administered to rats receiving a 2% cholesterol diet, for a period of fours days at daily doses which may vary from 5 to 25 mg/kg P.O. according to the compounds.

The animals were killed two hours after the last administration and there was then observed a decrease of the plasma cholesterol level up to 51%, by comparison with untreated animals.

Due to their pharmacological activity, the most interesting compounds are the compounds of formula I wherein R is hydrogen and Y is selected from the group consisting of a hydrogen atom, saturated and unsaturated hydrocarbon radicals up to $C_4$, more especially methyl, ethyl and allyl radicals, and a carboxymethyl radical.

The present invention also provides pharmaceutical compositions containing as active ingredient a compound of the formula I or a physiologically tolerable salt thereof, in admixture or conjunction with a pharmaceutically suitable carrier, such for example as distilled water, glucose, lactose, starch, talc, magnesium stearate, ethyl cellulose or cocoa butter.

The so-obtained pharmaceutical compositions are advantageously in unit dosage form and may contain from 50 to 250 mg of the active ingredient.

They may be in form of tablets, dragees capsules, suppositories or injectable or drinkable solutions and administered by oral, rectal or parenteral route at a dose of 50 to 250 mg 1 to 3 times a day.

The following examples illustrate the invention, the parts being by weight and the melting points being determined on the Kofler hot-plate.

EXAMPLE 1

4-(4-methoxy phenoxy) benzoyl chloride

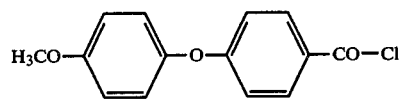

51 parts of 4-(4-methoxyphenoxy) benzoic acid and 75 parts of thionyl chloride were refluxed for two hours. After the elimination of the excess of the reagent under vacuo, the residue was treated twice with 100 parts of anhydrous benzene. The solvent was evaporated under vacuo and the remaining chloride was used without further purification.

EXAMPLES 2 to 6

The following compounds were prepared according to the process described in Example 1:
 (2) 4-phenoxy benzoyl chloride
 (3) 3-phenoxy benzoyl chloride
 (4) 2-phenoxy benzoyl chloride
 (5) 4-(4-methylphenoxy) benzoyl chloride
 (6) 4-(4-chlorophenoxy) benzoyl chloride

EXAMPLE 7 dl methyl N-[4-(4-methoxyphenoxy) benzoyl] valinate

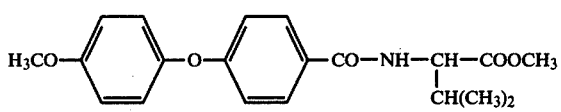

To a solution of 32.5 parts of dl methyl valinate hydrochloride in 300 parts of anhydrous dimethylformamide, there were added 42.4 parts of triethylamine. A solution of 55 parts of 4-(4-methoxyphenoxy) benzoyl chloride in 50 parts of anhydrous tetrahydrofuran was then poured to this reaction mixture for 20 minutes. The temperature progressively increased from 28° to 59° C. while the mixture was stirred for one hour and a half. The precipitate of triethylamine hydrochloride was filtered off and the residue concentrated under vacuo.

There were obtained 82 parts of dl methyl N-[4-(4-methoxy phenoxy) benzoyl]valinate which was used without further purification.

EXAMPLES 8 to 12

The following compounds were prepared according to the process described in Example 7:
- (8) dl methyl N-(4-phenoxybenzoyl) valinate.
- (9) dl methyl N-(3-phenoxybenzoyl) valinate.
- (10) dl methyl N-(2-phenoxybenzoyl) valinate.
- (11) dl methyl N-[4-(4-methylphenoxy) benzoyl] valinate.
- (12) dl methyl N-[4-(4-chlorophenoxy) benzoyl] valinate.

EXAMPLE 13 dl N-[4-(4-methoxyphenoxy) benzoyl]valine

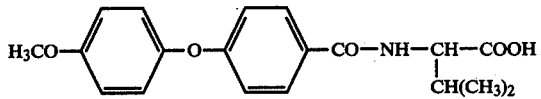

To a solution of 82 parts of dl methyl N-[4-(4-methoxyphenoxy) benzoyl]valinate in 300 parts of ethanol, there were added quickly 320 parts of a N aqueous solution of sodium hydroxide, and the reaction mixture was refluxed for two minutes.

Then, ethanol was evaporated under vacuo. The residue was acidified to pH 1 with 50 parts of a concentrated hydrochloric acid solution. After filtration, the precipitate was washed twice, each time with 100 parts of water, then suctioned off and dried. After recrystallization from 200 parts of benzene, there were obtained 52 parts of dl N-[4-(4-methoxyphenoxy) benzoyl]valine, M.P. 156° C.

EXAMPLES 14 to 18

The following compounds were prepared according to the process described in Example 13:
- (14) dl N-(4-phenoxybenzoyl) valine, M.P. 145° C. (benzene).
- (15) dl N-(3-phenoxybenzoyl) valine, M.P. 145-146° C. (benzene)
- (16) dl N-(2-phenoxybenzoyl) valine, M.P. 111° C. (acetonitrile)
- (17) dl N-[4-(4-methylphenoxy) benzoyl] valine, M.P. 173° C. (acetonitrile)
- (18) dl N-[d4-(4-chlorophenoxy) benzoyl] valine, M.P. 163-164° C. (acetonitrile)

EXAMPLE 19

β-[4-(4-methoxyphenoxy) benzoyl] propiononitrile

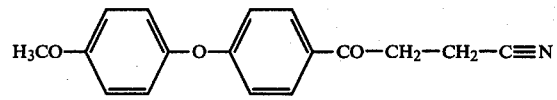

52 parts of dl N-[4-(4-methoxyphenoxy) benzoyl] valine and 62 parts of acetic anhydride were maintained at 80°-85° C. for five minutes. The solution thus obtained was concentrated in vacuo.

The residue was treated twice with each time 100 parts of benzene then the solvent was evaporated under vacuo. The residue was a slightly yellowish oil, which was dissolved in 100 parts of anhydrous methylene chloride and chilled to −20° C.

To this solution, 16 parts of freshly distilled acrylonitrile were added and the temperature was left to attain progressively 0° C. At this stage, a solution of 7.6 parts of triethylamine in 25 parts of methylene chloride was introduced while the reaction mixture was maintained at 0° C. After stirring at room temperature for 3 hours, the solvent was evaporated under vacuo. The residue was treated with 200 parts of ethyl acetate and washed successively with 150 parts and 75 parts of a 0.1 N hydrochloric acid solution. The organic layer was separated off, dried over anhydrous magnesium sulphate then concentrated in vacuo.

The residue was treated with 45 parts of a N solution of sodium hydroxide, then with 320 parts of methanol and 120 parts of tetrahydrofuran. After stirring at room temperature for 90 minutes, the precipitate was filtered, washed with water and dried. There were obtained 29.5 g of product, M.P. 86° C., which after one recrystallization from 160 parts of isopropanol gave 23.5 parts of pure β-[4-(4-methoxyphenoxy) benzoyl] propiononitrile, melting at 88° C.

EXAMPLES 20 to 24

The following compounds were prepared according to the process described in Example 19:
- (20) β-(4-phenoxy) benzoyl propiononitrile, M.P. 69° C. (isopropanol)
- (21) β-(3-phenoxy) benzoyl propiononitrile, M.P. 80° C. (isopropanol)
- (22) β-(2-phenoxy) benzoyl propiononitrile, M.P. 63°-64° C. (isopropanol)
- (23) β-[4-(4-chlorophenoxy) benzoyl] propiononitrile, M.P. 91° C. (isopropanol)
- (24) β-[4-(4-methylphenoxy) benzoyl] propiononitrile, M.P. 89°-90° C. (isopropanol)

EXAMPLE 25

2-[4-(4-methoxyphenoxy) phenyl] pyrrolidine

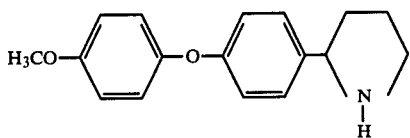

23 parts of β-[4-(4-methoxyphenoxy) benzoyl] propiononitrile in solution in 200 parts of dimethylformamide were reduced by hydrogen in presence of 10 parts of Raney Nickel at a pressure of 8 kg/cm², and a temperature of 60° C. The reduction was achieved in 5 hours. After filtration and washing of the catalyst, the filtrate was distilled. There were obtained 15 parts of product, B.P./0.1 mm Hg:172°–174° C., which gave 12.5 parts of 2-[4-(4-methoxyphenoxy) phenyl] pyrrolidine hydrochloride, M.P. 157° C. (acetone).

EXAMPLES 26 to 30

The following compounds were prepared according to the process described in Example 25.

(26) 2-(4-phenoxyphenyl) pyrrolidine, B.P./0.6 mm Hg: 164°–165° C., M.P. of its hydrochloride:171°–172° C. (acetonitrile)

(27) 2-(3-phenoxyphenyl) pyrrolidine, B.P./0.4 mm Hg: 153°–155° C., M.P. of its hydrochloride:163° C. (isopropanol).

(28) 2-(2-phenoxyphenyl) pyrrolidine, B.P./0.3 mm Hg: 145°–147° C., M.P. of its hydrochloride: 140° C. (acetonitrile).

(29) 2-[4-(4-chlorophenoxy) phenyl]) pyrrolidine, B.P./0.3 mm Hg: 155°–160° C., M.P. of its hydrochloride:180° C. (acetonitrile)

(30) 2-[4-(4-methylphenoxy) phenyl] pyrrolidine, B.P./0.1 mm Hg: 155°–157° C. M.P. of its acid fumarate:132°–133° C. (isopropanol).

EXAMPLE 31

1-methyl-2-(4-phenoxyphenyl) pyrrolidine

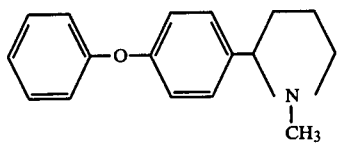

113.5 parts of 2-(4-phenoxyphenyl) pyrrolidine, 115 parts of a solution at 40% of formaldehyde and 145 parts of formic acid at 98% were refluxed for 10 hours. After cooling, the mixture was acidified with 600 parts of a 4 N hydrochloric acid solution then concentrated in vacuo.

The residue was treated with 950 parts of water, then extracted twice with each time 300 parts of ether. The solution was dried over Mg SO₄, then the solvent was evaporated. There were obtained 109 parts of 1-methyl-2-(4-phenoxyphenyl) pyrrolidine, B.P./0.8 mm Hg: 157°–159° C., $n_D^{24.5}$: 1.5692, M.P. of its hydrochloride: 161°–162° C. (ethylacetate/isopropanol).

EXAMPLES 32 to 36

The following compounds were prepared according to the process described in Example 31.

(32) 1-methyl (3-phenoxyphenyl) pyrrolidine, M.P. of its acid fumarate: 113°–115° C. (acetonitrile).

(33) 1-methyl (2-phenoxyphenyl) pyrrolidine.

(34) 1-methyl-2-[4-(4-methylphenoxy) phenyl] pyrrolidine, B.P./0.9 mm Hg: 167°–170° C., M.P. of its acid fumarate: 121° C. (acetonitrile).

(35) 1-methyl-2-[4-(4-chlorophenoxy) phenyl] pyrrolidine, B.P./0.2 mm Hg: 150°–152° C.

(36) 1-methyl-2-[4-(4-methoxyphenoxy) phenyl] pyrrolidine.

EXAMPLE 37

1-allyl-2-(4-phenoxyphenyl) pyrrolidine

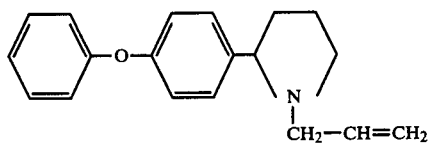

8 parts of 2-(4-phenoxyphenyl) pyrrolidine, 3.3 parts of triethylamine, 4 parts of allyl bromide and 70 parts of toluene were refluxed for 5 hours. After cooling and filtration, there were obtained by distillation 7.7 parts of 1-allyl-2-(4-phenoxyphenyl) pyrrolidine, B.P./0.2 mm Hg: 148°–150° C., $n_D^{26}$=1.5695, M.P. of its acid fumarate: 115°–116° C. (isopropanol/ether).

EXAMPLES 38 to 42

The following compounds were prepared according to the process described in Example 37.

(38) 1-allyl-2-(3-phenoxyphenyl) pyrrolidine.

(39) 1-allyl-2-(2-phenoxyphenyl) pyrrolidine.

(40) 1-allyl-2-[4-(4-chlorophenoxy) phenyl] pyrrolidine.

(41) 1-allyl-2-[4-(4-methylphenoxy) phenyl] pyrrolidine.

(42) 1-allyl-2-[4-(4-methoxyphenoxy) phenyl] pyrrolidine.

EXAMPLE 43

1-ethyl-2-(4-phenoxyphenyl) pyrrolidine

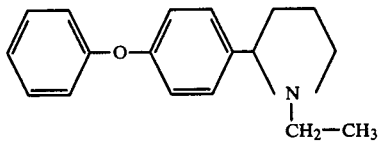

To a solution of 10 parts of 2-(4-phenoxyphenyl) pyrrolidine in 200 parts of anhydrous ether and 4.2 parts of triethylamine, there was added a solution of 3.3 parts of acetyl chloride in 30 parts of ether. The reflux was maintained for one hour, then the reaction mixture was filtered off on cooling and the filtrate was distilled. There were obtained 13 parts of 1-acetyl-2-(4-phenoxyphenyl) pyrrolidine.

These 13 parts were dissolved in 150 parts of anhydrous ether, and the so-obtained solution was added in 90 minutes to a suspension of 3.5 parts of lithium aluminium hydride in 80 parts of ether. The mixture was refluxed for 4 further hours. After hydrolysis of the mixture, the precipitate was filtered off. There were obtained 9 parts of 1-ethyl-2-(4-phenoxyphenyl) pyrrolidine, B.P./0.9 mm Hg: 146°–148° C., $n_D^{24}$: 1.5620, M.P. of its acid fumarate: 142°–143° C. (ethyl acetate).

EXAMPLES 44 to 48

The following compounds were prepared according to the process described in Example 43:
(44) 1-ethyl-2-(3-phenoxyphenyl) pyrrolidine.
(45) 1-ethyl-2-(2-phenoxyphenyl) pyrrolidine. (46) 1-ethyl-2-[4-(4-chlorophenoxy) phenyl] pyrrolidine.
(47) 1-ethyl-2-[4-(4-methylphenoxy) phenyl] pyrrolidine.
(48) 1-ethyl-2-[4-(4-methoxyphenoxy) phenyl] pyrrolidine.

EXAMPLE 49

1-carboxymethyl-2-(4-phenoxyphenyl) pyrrolidine

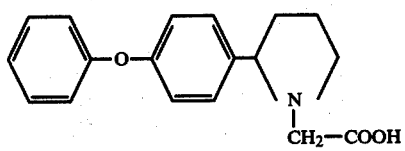

To a solution of 23.9 parts of 2-(4-phenoxyphenyl) pyrrolidine in 80 parts of anhydrous benzene, there were quickly added 8.35 parts of ethyl bromacetate. The reaction mixture was then refluxed for 4 hours. After cooling and filtration, the residue was treated with 50 parts of water and 100 parts of ether. After decantation, then distillation, there were obtained 11.3 parts of 1-ethoxycarbonylmethyl-2-(4-phenoxyphenyl) pyrrolidine, B.P./0.1 mm Hg: 165° C., $n_D^{23}$: 1.5524.

11 parts of the so-obtained 1-ethoxycarbonylmethyl-2-(4-phenoxyphenyl) pyrrolidine, 50 parts of a N solution of sodium hydroxide and 40 parts of ethanol were refluxed for one hour. The reaction mixture was concentrated in vacuo, acidified with 50 parts of a N solution of hydrochloric acid, treated with 80 parts of anhydrous isopropanol, then concentrated again.

After treatment with hydrochloric acid and recrystallization from acetone, there were obtained 1-carboxymethyl-2-(4-phenoxyphenyl) pyrrolidine hydrochloride, melting at 114° C.

EXAMPLES 50 to 54

The following compounds were prepared according to the process described in Example 49:
(50) 1-carboxymethyl-2-(3-phenoxyphenyl) pyrrolidine.
(51) 1-carboxymethyl-2-(2-phenoxyphenyl) pyrrolidine.
(52) 1-carboxymethyl-2-[4-(4-chlorophenoxy) phenyl] pyrrolidine.
(53) 1-carboxymethyl-2-[4-(4-methylphenoxy) phenyl] pyrrolidine.
(54) 1-carboxymethyl-2-[4-(4-methoxyphenoxy) phenyl] pyrrolidine.

EXAMPLE 55

1-β-hydroxyethyl-2-(4-phenoxyphenyl) pyrrolidine

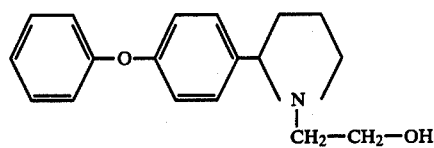

12 parts of 2-(4-phenoxyphenyl) pyrrolidine, 2.2 parts of ethylene oxide and 1 part of water were heated at 80° C. for 5 hours. After cooling, there were obtained 8 parts of 1-β-hydroxyethyl-2-(4-phenoxyphenyl) pyrrolidine, B.P./0.3 mm Hg: 179°–180° C.

EXAMPLES 56 to 60

The following compounds were prepared according to the process described in Example 55:
(56) 1-β-hydroxyethyl-2-(3-phenoxyphenyl) pyrrolidine.
(57) 1-β-hydroxyethyl-2-(2-phenoxyphenyl) pyrrolidine.
(58) 1-β-hydroxyethyl-2-[4-(4-chlorophenoxy) phenyl] pyrrolidine. p1 (59) 1-β-hydroxyethyl-2-[4-(4-methylphenoxy) phenyl]pyrrolidine.
(60) 1-β-hydroxyethyl-2-[4-(4-methoxyphenoxy) phenyl] pyrrolidine.

We claim:
1. A compound having the formula:

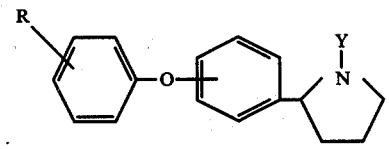

wherein:
—R is selected from the group consisting of hydrogen, halogen, alkyl and alkoxy of 1 to 4 carbon atoms inclusive, and trifluoromethyl;
—Y is selected from the group consisting of hydrogen, saturated and unsaturated hydrocarbon radical of from 1 to 4 carbon atoms inclusive, hydroxyethyl, hydroxypropyl and carboxymethyl; and physiologically tolerable acid addition salts thereof.

2. A compound of claim 1 of the formula I wherein R is hydrogen and Y is selected from the group consisting of hydrogen, saturated and unsaturated hydrocarbon radicals up to $C_4$ inclusive, and carboxymethyl, and physiologically tolerable acid addition salts thereof.

3. A compound of claim 1 which is 2-(2-phenoxyphenyl) pyrrolidine.

4. A compound of claim 1 which is 1-methyl-2-(4-phenoxyphenyl) pyrrolidine.

5. A compound of claim 1 which is 1-allyl-2-(4-phenoxyphenyl) pyrrolidine.

6. A compound of claim 1 which is 1-ethyl-2-(4-phenoxyphenyl) pyrrolidine.

7. A compound of claim 1 which is 1-carboxymethyl-2-(4-phenoxyphenyl) pyrrolidine.

8. A pharmaceutically administrable dosage unit for the treatment lipid metabolism disorders of animals afflicted therewith containing from 50 to 250 mg of a compound of claim 1 and a suitable pharmaceutically acceptable carrier.

9. A method for treating a animal body affflicted with lipid-metabolism disorders comprising the steps of administering an amount of a compound of claim 1 which is effective for the alleviation of the said condition.

* * * * *